United States Patent [19]

Fujimura et al.

[11] Patent Number: 5,506,264
[45] Date of Patent: Apr. 9, 1996

[54] ZINC TRANEXAMATE COMPOUNDS

[75] Inventors: Hajime Fujimura, Kyoto; Takahiro Yabuuchi, Takarazuka; Teruo Tanaka, Kyoto, all of Japan

[73] Assignee: Zaidan Hojin Seisan Kaihatsu Kaguki Kenkyusho, Kyoto, Japan

[21] Appl. No.: 356,282
[22] PCT Filed: Jun. 21, 1993
[86] PCT No.: PCT/JP93/00852
   § 371 Date: Dec. 20, 1994
   § 102(e) Date: Dec. 20, 1994
[87] PCT Pub. No.: WO94/00417
   PCT Pub. Date: Jan. 6, 1994

[30] Foreign Application Priority Data

Jun. 23, 1992 [JP] Japan .................. 4-189831

[51] Int. Cl.⁶ .................. A61K 31/315; C07F 3/06
[52] U.S. Cl. .................. 514/494; 514/925; 514/926; 556/132; 556/134
[58] Field of Search .................. 556/132, 134; 514/494, 925, 926

[56] References Cited

FOREIGN PATENT DOCUMENTS 0079872  5/1983  European Pat. Off. .
0163813  8/1985  Japan .
60-163813 8/1985  Japan .

OTHER PUBLICATIONS

Database WPI, week 8220, Derwent Publications Ltd., London, GB AN82–40390E & JP–A–57–059–847 (Hisamitsu Pharm) Abstract (1982).

*Primary Examiner*—Porfirio Nazario-Gonzales
*Attorney, Agent, or Firm*—Burgess, Ryan and Wayne

[57] ABSTRACT

The present invention is concerned with the zinc tranexamate represented by the formula:

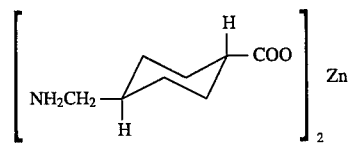

or its pharmacologically acceptable organic acid salts. The zinc compounds of the present invention, when given in smaller doses than tranexamic acid and cetraxate hydrochloride, exhibit anti-inflammatory and anti-ulcer activities, and are tasteless and odorless, thus being easy to be administered; in particular, the organic acid salts are water-soluble and can be processed into the liquid dosage forms of injectable solution and liquid preparations for external uses.

6 Claims, No Drawings

ZINC TRANEXAMATE COMPOUNDS

This application is a request for U.S. examination filed under 35 U.S.C. §371 of International application No. PCT/JP93/00852 filed on Jun. 21, 1993.

TECHNICAL FIELD

The present invention relates to a novel zinc tranexamate compound and its pharmacologically acceptable organic acid salts, to a process for producing the same and to anti-inflammatory and anti-ulcer agents which individually contain the same as an active ingredient.

BACKGROUND ART

Tranexamic acid inhibits the bonding of plasminogen or plasmin with fibrin to lower their fibrinolytic activities, and thus suppress bleeding. By way of such a mechanism, the compound suppresses vascular fragility and also develops anti-allergic and anti-inflammatory activities. Specifically, the compound is considered to be effective against hyperemia, reddening, swelling and ache accompanying by tonsillitis, pharyngo-laryngitis, stomatitis, aphtha in the mucosa of the mouth. However, no report has been made so far on the anti-gastritic and anti-peptic/duodenal ulcer activities of tranexamic acid, with no paper being published on the synthesis and pharmacological activities of the zinc tranexamate compound.

The present inventors, with a specific view to the development of an excellent anti-ulcer agent and anti-gastritis agent, synthesized a large number of zinc compounds and investigated their therapeutic effects, and, as a result, found that zinc tranexamate, among others, exhibits distinctly marked therapeutic activities. The finding was followed by further research work, leading to the completion of the present invention.

DISCLOSURE OF THE INVENTION

The present invention relates to a novel zinc tranexamate compound as represented by the formula (I):

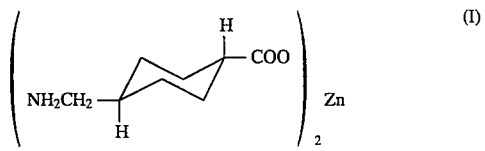

and its pharmacologically acceptable salts with organic acids, to a process for producing the same and to an anti-inflammatory agent and anti-ulcer agent which individually contain the same as an active ingredient.

The compound of formula (I) is produced by reacting a compound of formula (II):

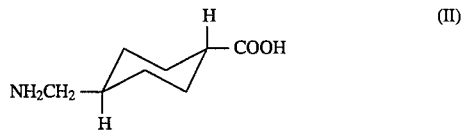

with an alkali agent and zinc compound. Referring to the alkali agent, there may preferably be used alkali metal alcoholates such as sodium methylate, sodium ethylate, potassium methylate, potassium ethylate and potassium t-butoxide, while as the zinc compound, use is normally made of zinc salts soluble in a reaction solvent such as zinc acetate, zinc chloride, zinc bromide and zinc iodide, but other zinc compounds may be utilized. The reaction is preferably carried out in a water-free solvent and is normally conducted in a suitable solvent such as methanol and ethanol at room temperature or under heating for several minutes to several hours, and after the conclusion of the reaction, the compound of the formula (I) that crystallizes out can be purified by conventional means.

The present invention is understood to cover pharmacologically acceptable organic-acid salts of the compound of the formula (I), and their examples include salts with aliphatic carboxylic acids, such as acetic acid; glycolic acid, lactic acid, succinic acid, malic acid, tartaric acid, maleic acid and fumaric acid; amino acids; such as aspartic acid and glutamic acid; and aromatic carboxylic acids such as benzoic acid and phthalic acid.

Organic-acid salts of the compound (I) are obtained, for example, by adding the compound (I) to an organic acid dissolved in methanol or another anhydrous solvent to allow them to react.

The compound of the formula (I) according to the present invention and its organic-acid salts possess excellent anti-aphtha activity, anti-gastric/duodenal ulcer activity, and anti-gastritis/duodenitis activity, while they exhibit lower toxicity. The compound of the formula (I) and its organic-acid salts can be administered orally or parenterally either per se or after being admixed with pharmacologically acceptable, appropriate excipients, carriers, diluents, etc. to process into various dosage forms such as tablets, capsules, granules and powders. Also, the organic acid salts of the compound of the formula (I), being soluble in water, find wide application in a great variety of fields in various dosage forms such as injectable solutions, transfusions, syrups, ophthalmic solutions and dental disease treatment agents, as well as liquid preparations for external use such as nasal drops and inhalants. The dosage amount varies with the symptoms, age and body weight of patients, route of administration and the like, and the compound can usually be administered to human adults orally at a daily dose of 300 to 2,000 mg, divided into three to four doses.

Described below are Examples and Test Examples of this invention to illustrate the present invention in more detail.

EXAMPLES

EXAMPLE 1

Dissolved in 80 ml of methanol was 7.9 g (50 mmole) of tranexamic acid, and 9.8 ml (50 mmole) of a 28% solution of sodium methylate in methanol, followed by stirring at 50° C. for 15 min. After cooling, the reaction solution was admixed with a solution of 5.5 g of zinc acetate dehydrate (25 mmole) in 60 ml of methanol, followed by stirring at room temperature for 30 min. The precipitate which deposited was recovered by filtration, washed with methanol and dried under reduced pressure to give 9.5 g of zinc tranexamate monohydrate in the form of a colorless powder. Yield of 96.0%, m.p.>250° C.

Elemental analysis (%): $C_{16}H_{30}N_2O_5Zn$ Calcd., C:48.55, H:7.64, N:7.08, Zn:16.52 Found , C:48.73, H:7.36, N:7.05, Zn:16.50 IR (KBr, $cm^{-2}$ ); 3409, 3321, 3243, 2928, 2859, 1568 1419, 1352, 1334, 1288, 1236, 1169, 1115, 1027.

EXAMPLE 2

Dissolved in 20 ml of methanol was 2.68 g (20 mmole) of L-malic acid, and 7.92 g (20 mmole) of zinc tranexamate monohydrate was added to the resultant solution, followed by stirring at room temperature for 30 min. The methanol was removed under reduced pressure to give the L-malic acid salt of zinc tranexamate monohydrate in the form of a colorless powder. m.p. 204° C. (decomp.). 1 g of the compound dissolves in 2 ml of water.

Elemental analysis (%): $C_{20}H_{36}N_2O_{10}Zn$ Calcd., C:45.33, H:6.85, N:5.29, Zn:12.33 Found , C:45.61, H:6.73, N:5.20, Zn:12.06 IR (KBr, cm$^{-1}$); 3439, 2934, 2864, 2709, 2611, 2209, 1636, 1540, 1452, 1385, 1330, 1257, 1228, 1197. 1163, 1090, 1032, 1010.

Test Example 1. Anti-ulcer test:

Male rats of Sprague-Dawley strain (supplied by Charles-River Co., SPE) weighing 220 to 280 g were fasted for 24 hours and employed in the experiment, whereby the rats were allowed free access to water for the first 22 hours, with no water being given for the remaining 2 hours.

The test compound was suspended in 0.5% aqueous carboxymethylcellulose solution and the suspension was given to the test animals at a dose of 1 ml/200 g body weight, with the solvent alone being applied as a control at the same dose.

(1) Stomach injury with hydrochloric acid/ethanol:

Rats were treated by oral administration of hydrochloric acid/ethanol (containing 0.15 mole hydrochloric acid solution in 80% ethanol) at a dose of 1 ml/200 g body weight and sacrificed with ether 1 hour later, and the stomachs and duodena were isolated, followed by removal of the contents from the duodena. After the cardiac orifices were ligated, 2% formalin solution was injected in 8 ml portion into the stomachs through the duodenum, and the pyloric sphincters were ligated, followed by immersion into the same solution for 10 min to perform slight fixation (hereinafter referred to as "formalin treatment"). The stomachs were incised along the greater curvature, and individual injuries (erosions) generated in the glandular portion of each stomach were measured in length (mm) under microscope for anatomy (10 fold magnification), with the total sum per rat of measured injury lengths being calculated. The test compound was given to the animals orally 1 hour before administration of hydrochloric acid/ethanol. The results are shown in Table 1.

TABLE 1

| Test compound | Dose (mg/kg) | No. of animals | Ulcer coefficient (mm) mean ± S.E. | Suppression % |
|---|---|---|---|---|
| Non-treated | — | 8 | 78.4 ± 21.1 | — |
| Zinc tranexamate monohydrate | 50 | 8 | 14.8 ± 4.5* | 81.1* |
| Tranexamic acid | 50 | 8 | 70.5 ± 20.1 | 10.1 |
| Cetraxate hydrochloride | 50 | 8 | 46.3 ± 7.6 | 40.9 |

Notes: *, Level of significance, p<0.05.

(2) Stomach injury through water-immersion constraint stress:

The rats were stress-loaded by soaking the animals placed in a stress cage of Univ. of Tokyo type up to the xiphoid in a water tank at 23° C. and they were taken out of the tank 8 hours later and sacrificed with ether. The stomachs were isolated and treated with formalin, and individual injuries formed in the glandular portion of the stomach were measured in length (mm), with the total sum per rat of the measured injury lengths being calculated. The test compound was given to the test animals orally immediately before the stress-loading. The results are shown in Table 2.

TABLE 2

| Test compound | Dose (mg/kg) | No. of animals | Ulcer coefficient (mm) mean ± S.E. | Suppression % |
|---|---|---|---|---|
| Non-treated | — | 8 | 52.8 ± 9.8 | — |
| Zinc tranexamate monohydrate | 50 | 8 | 22.3 ± 8.4* | 57.8* |
|  | 50 | 8 | 22.3 ± 8.4* | 57.8* |
| Tranexamic acid | 50 | 8 | 46.5 ± 8.4 | 11.9 |
| Cetraxate hydrochloride | 50 | 8 | 32.0 ± 8.4 | 39.4 |

Notes: *, Level of significance, p<0.05.

Zinc tranexamate monohydrate of the present invention, in the anti-ulcer test, exhibited improved suppressory activity as compared with the control, or tranexamic acid and cetraxate hydrochloride.

2. Acute toxicity test:

Male ddy strain mice (weighing 23 to 26 g) used in the experiment were divided into groups each consisting of 3 heads and treated by oral administration of the test compound suspended with powdered gum arabic, followed by observation for any abnormalities over a 3 day period to find the number of dead animals. As a result, zinc tranexamate monohydrate at doses up to 1,200 mg/kg did not cause any animal to die, thus leading to confirm that the compound of the present invention shows an extremely enhanced degree of safety in contrast with its effective doses. The results are shown in Table 3.

TABLE 3

| Test compound | Dose (mg/kg) | Nd/No* |
|---|---|---|
| Zinc tranexamate monohydrate | 600 | 0/3 |
|  | 1,200 | 0/3 |
| Tranexamic acid | 600 | 0/3 |
|  | 1,200 | 0/3 |
| Cetraxate hydrochloride | 600 | 0/3 |
|  | 1,200 | 0/3 |

Note: *, Nd = No. of dead animals
No = Total No. of experimental animals

Industrial Applicability

As is evident from the test results, tranexamic acid did not produce any marked effects, and this finding is considered to be natural in the light of the fact that tranexamic acid is administered orally at large doses as much as 750 mg to 2,000 mg. Cetraxate hydrochloride, which is the most effective of the currently commercialized mucosal protective factor reinforcing preparations and finds frequent application, is administered at levels of 600 to 800 mg a day, although it contains tranexamic acid in the molecule. In contrast, the compound of the present invention possesses distinctly improved activity over said cetraxate and can therefore be expected to produce satisfactory effects at daily doses of 300 to 400 mg, while the compound offers the advantage that it is tasteless and odorless, thus being easier to take. In addition, organic acid salts of the compound of the present invention are soluble in water and can find application in a wide variety of fields as an injectable

We claim:

1. A zinc tranexamate compound represented by the formula:

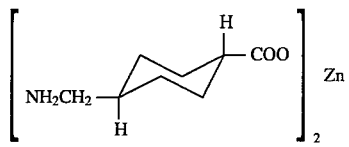

or its pharmacologically acceptable organic-acid salt.

2. A process for producing a zinc tranexamate compound represented by the formula:

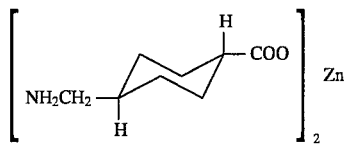

or its pharmacologically acceptable organic-acid salt, characterized in that said process comprises reacting tranexamic acid with an alkali agent and zinc compound, followed, if required, by further reaction with an organic acid.

3. An anti-inflammatory agent in the alimentary tract and anti-ulcer agent which individually contain as an active ingredient a zinc tranexamate compound represented by the formula:

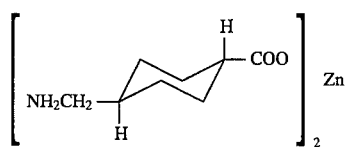

or its pharmacologically acceptable organic-acid salt.

4. A pharmaceutical composition comprised of a therapeutically effective amount of the compound of claim 1 and a pharmaceutically acceptable carrier.

5. A method for treating ulcers in a patient which comprises administering to said patient a therapeutically effective amount of the pharmaceutical composition of claim 4.

6. A method for treating a patient suffering from an inflammatory disease in the alimentary tract which comprises administering to such patient a therapeutically effective amount of the pharmaceutical composition of claim 4.

* * * * *